(12) United States Patent
Klupt

(10) Patent No.: US 6,766,549 B2
(45) Date of Patent: Jul. 27, 2004

(54) TOOTHBRUSH SYSTEM WITH A THREE-DIMENSIONAL BRUSHING ACTION AND FLUID IRRIGATION

(76) Inventor: Michael F. Klupt, 7 Thistledell Ct., Owings Mills, MD (US) 21117

( * ) Notice: Subject to any disclaimer, the term of this patent is extended or adjusted under 35 U.S.C. 154(b) by 294 days.

(21) Appl. No.: 10/123,412

(22) Filed: Apr. 17, 2002

(65) Prior Publication Data

US 2002/0152565 A1 Oct. 24, 2002

Related U.S. Application Data

(60) Provisional application No. 60/284,919, filed on Apr. 20, 2001.

(51) Int. Cl.$^7$ .......................... A46B 13/04; A46B 11/02; A46B 7/08
(52) U.S. Cl. .............................. 15/22.2; 15/22.1; 15/29; 433/84; 433/80; 433/125; 601/162
(58) Field of Search ................................ 15/29, 24, 28, 15/23, 22.1, 22.2; 601/162, 163, 165, 158, 51; 433/216, 125, 89, 142, 124, 122, 126, 131, 132, 99, 82, 87, 83, 85, 116, 166

(56) References Cited

U.S. PATENT DOCUMENTS

| 2,184,212 A | | 12/1939 | Davidson |
| 2,400,912 A | * | 5/1946 | Britt et al. ............... 433/82 |
| 2,546,754 A | | 3/1951 | Jones |
| 3,022,789 A | | 2/1962 | Rallis et al. |
| 3,195,537 A | * | 7/1965 | Blasi ....................... 601/114 |
| 3,261,367 A | | 7/1966 | Pickering |
| 3,509,874 A | * | 5/1970 | Stillman .................. 601/163 |
| 3,549,268 A | | 12/1970 | Casselman |
| 3,825,354 A | | 7/1974 | Rallis |
| 3,892,237 A | | 7/1975 | Steiner |
| 4,296,071 A | | 10/1981 | Weiss et al. |
| 4,332,497 A | | 6/1982 | Rodriguez |
| 4,467,822 A | | 8/1984 | Blackwell |
| 4,583,563 A | | 4/1986 | Turner |
| 4,671,259 A | * | 6/1987 | Kirchner ................. 601/163 |
| 4,759,383 A | | 7/1988 | Phillips |
| 4,950,247 A | | 8/1990 | Rosenblatt |
| 4,955,567 A | | 9/1990 | Longhurst |
| 4,963,046 A | | 10/1990 | Eguchi |
| 5,301,381 A | | 4/1994 | Klupt |
| 5,321,866 A | | 6/1994 | Klupt |
| 5,623,746 A | * | 4/1997 | Ichiro ....................... 15/22.2 |

* cited by examiner

Primary Examiner—Gary K. Graham
(74) Attorney, Agent, or Firm—Rosenberg, Klein & Lee

(57) ABSTRACT

A toothbrush system using a combination of mechanical force and fluid dynamics to increase the efficiency of plaque removal from the teeth and gums. The toothbrush includes a head unit with an irrigator nozzle and a hydraulically actuated and continuously variable bristle platform which negotiates the complex surface geometry found in the mouth of a user. The irrigation nozzle is powered by the pulsing of an anti-microbial irrigant which gives the toothbrush head unit the distinguishing ability of being able to "feel" the contour of the teeth and to "find" the spaces between them. Once the sensing irrigator nozzle finds the spaces between the teeth, it extends into the area, and releases the anti-microbial liquid directly into the space. The configured bristle tufts of the head unit automatically adjust their position for cleaning under the gum line, between the teeth, as well as flat surfaces.

20 Claims, 10 Drawing Sheets

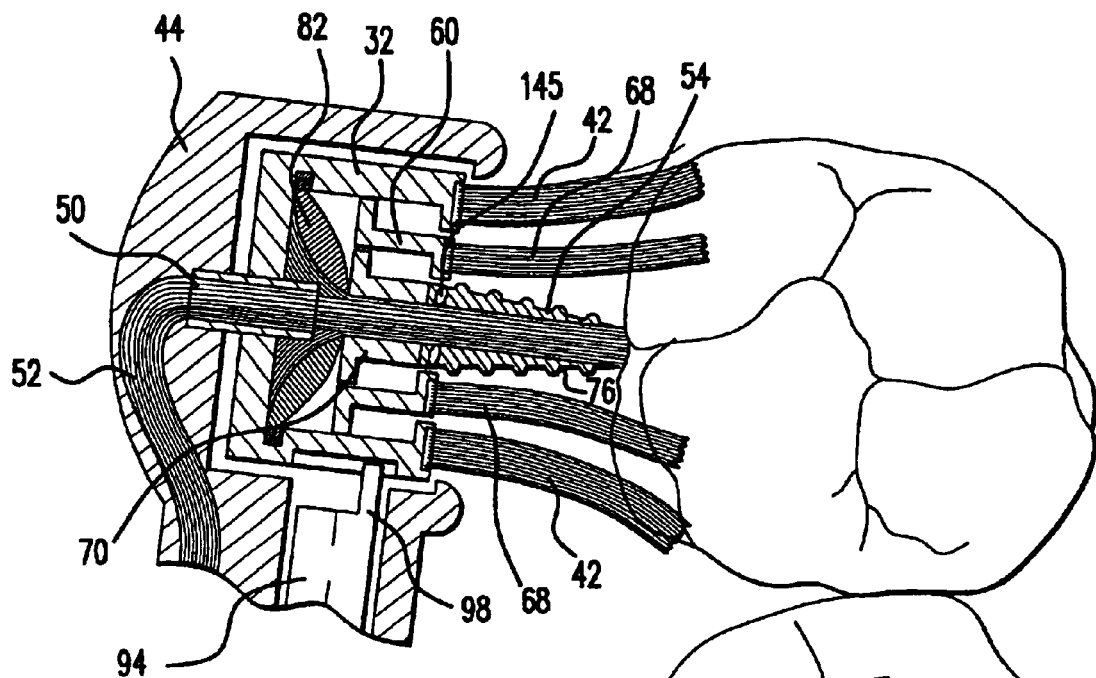
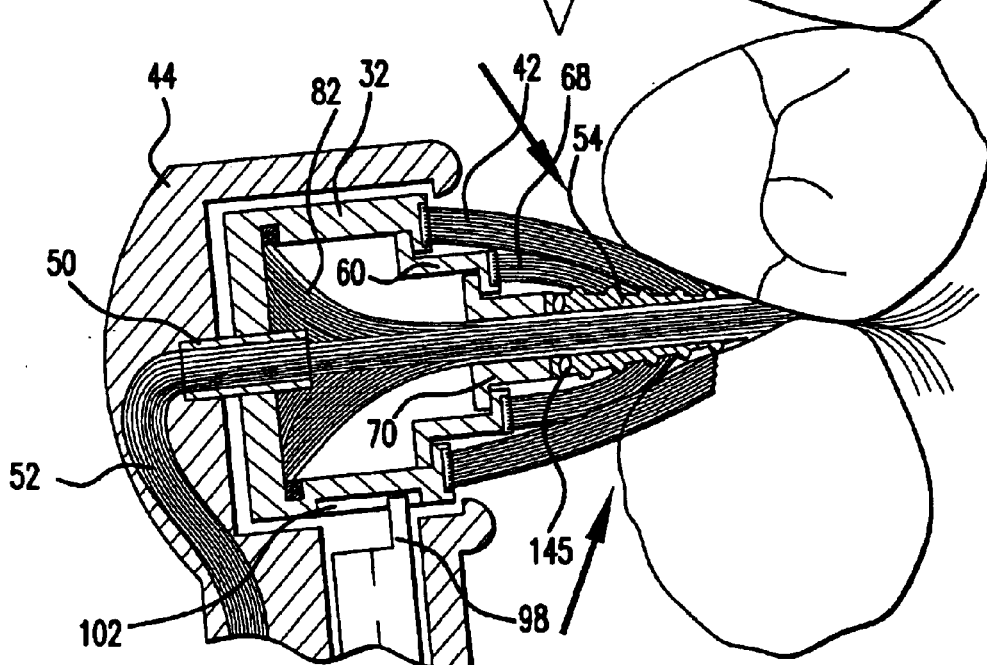
FIG.8A
FIG.8B

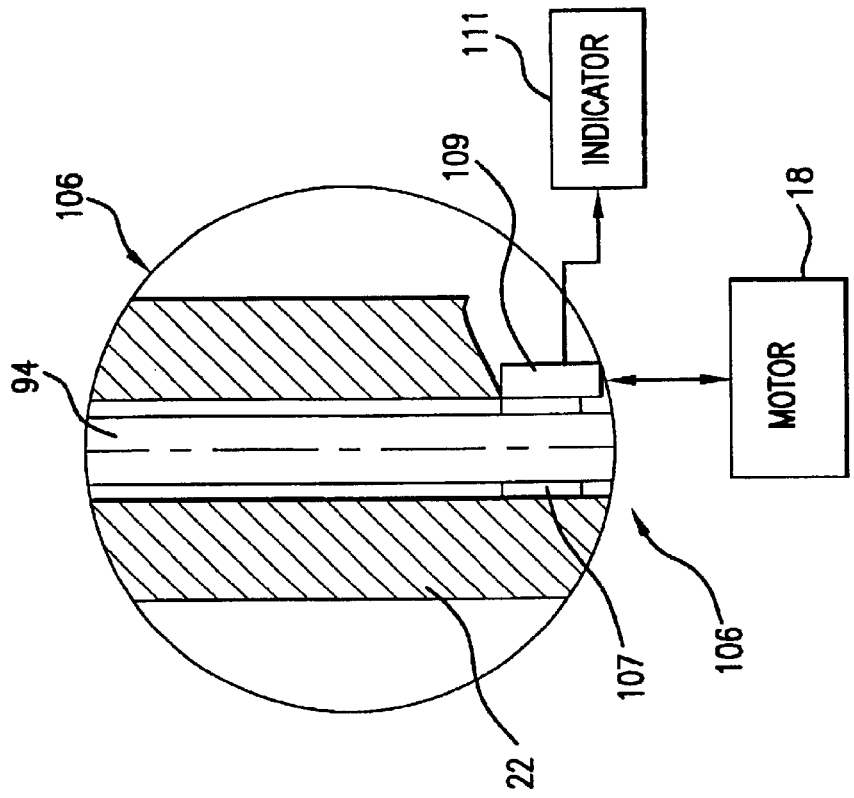
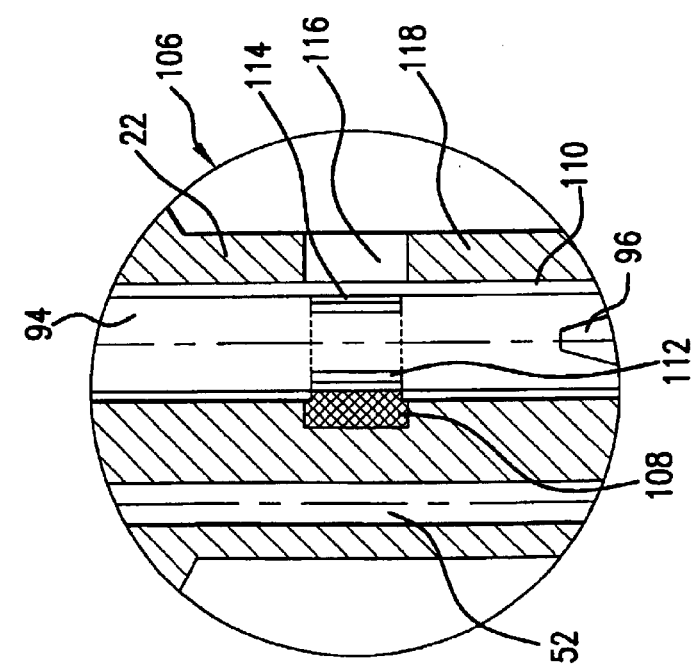

TOOTHBRUSH SYSTEM WITH A THREE-DIMENSIONAL BRUSHING ACTION AND FLUID IRRIGATION

REFERENCE TO RELATED APPLICATIONS

This Patent Application is based upon Provisional Patent Application Serial No. 60/284,919, filed on 20 Apr. 2001.

FIELD OF THE INVENTION

This invention pertains to a portable toothbrush system which is adapted to contain and apply all of the necessary brushing motions in combination with application of cleansing and anti-microbial irrigant liquid, fluids which may include astringent, fluoride, tartar control, microbial, and/or whitening agents as well as prescriptions or over-the-counter medications, during normal operational modes when a user is brushing his or her teeth.

Additionally, in further overall concept, the present invention is directed to a portable toothbrush system having a replaceable toothbrush head which utilizes a unique combination of mechanical force and fluid dynamics to increase the efficiency and efficacy of plaque removal from teeth, gums, as well as between teeth.

Still further, the present invention is directed to a disposable toothbrush head which uses a hydraulically actuated/continuously variable telescoping bristle platform to negotiate the complex surface geometry found in the mouth. A telescopic irrigation nozzle is powered by the fluid pulsations of the anti-microbial irrigant which gives the toothbrush head the distinguishing ability of being able to "feel" the contour of the teeth and "find" or locate spaces between the teeth. In particular, the "sensing" irrigation nozzle initially finds the space between the teeth containing the most destructive plaque deposits. The nozzle then extends into the area space and releases the anti-microbial irrigant, which is then followed by retraction back to the rest of the bristle platform. The textured surface of the irrigation nozzle also mechanically removes plaque between teeth.

The present invention is further directed to a replaceable toothbrush head which permits simultaneous brushing action of the bristles and angular articulation and telescoping motion for brushing various surfaces of the teeth. In addition to the brushing action of the bristles and cleansing action of the textured irrigation nozzle, the toothbrush head permits telescoping motion of the irrigation nozzle for delivery of the anti-microbial irrigant into the space between the teeth. To even further improve the overall performance of the toothbrush, the bristle tufts have unique geometric configurations which force the bristles to diverge or converge in response to a complex geometry of the surface of the teeth. In this manner, the toothbrush head automatically adjusts the position of the bristle tufts for cleaning under the gum line or between the teeth.

In particular, the invention relates to a toothbrush system having:

a handle member with an internal chamber defined therein which contains a fluid (i.e., an anti-microbial irrigant or other cleansing or whitening fluid, etc.), a head member secured to the handle member, and a head unit positioned at the end of the head member opposingly positioned with respect to the handle member. The head unit includes a bristle platform with the bristles arranged in circumferential disposition with regard to the central axis of the head unit. The head unit further includes a hydraulically biased irrigating member which is fluidly coupled to the internal chamber of the handle member through a fluid conduit extending through the head member. The irrigating member includes an irrigator nozzle reciprocating between a retracted and extended position thereof depending on the surface geometry of the mouth. In the extended position, which is the case when the irrigator nozzle "finds" the space between the teeth or any other concave surface with the biggest deposits of the plaque, the irrigator nozzle releases the fluid into the mouth of a user, thus exposing the problem areas to the thorough treatment by the irrigant fluid.

PRIOR ART

Toothbrush systems which allow for the rotation of the toothbrush bristles are known in the art. The prior art known to the Applicant includes U.S. Pat. Nos. 4,963,046; 3,022,789; 3,825,354; 3,261,367; 4,332,497; 4,955,567; 4,759,383; 4,296,071; 3,549,268; 4,467,822; 4,583,563; 2,184,212; 4,950,247; 2,546,754; and, 3,892,237.

In some prior art systems such as that shown in U.S. Pat. No. 4,963,046, there are cartridge-type storage portions which are removably connected to the toothbrush system. Additionally, such prior art systems show communication passages for supplying orally applied fluid from the storage to the bristle implanted surface on the brush base. However, such prior art systems do not provide for the pulsating type of cleansing liquid flow which is advantageous to the removal of contaminants within the mouth of a user. Additionally, such prior art systems do not show the simultaneous pulsating fluid flow in combination with the multiplicity of rotational planes for the bristles during use.

Other prior art systems such as that shown in U.S. Pat. No. 3,022,789 provide for injector-type toothbrushes for receiving toothpaste from a high pressure system such as an aerosol bomb. Such provide for a hollow type toothbrush with a detachable injector, however, such do not provide for the combination of bristle rotations in a plurality of planes with the pulsating fluid flow of the subject system.

In still other prior art systems, such as those shown in U.S. Pat. No. 3,825,354 describe toothbrush adaptors for aerosol containers. However, such do not provide for the advantageous pulsating fluid flow as is necessary to the subject system.

Basically, there are prior art systems which include rotating heads with bristles which are advantageous for application to specific gum or tooth areas and include heads that oscillate through an approximate 90° angle. However, although sufficient for cleaning generally flat surfaces, such prior art systems are disadvantageous for arcuate surfaces of teeth and do not provide adequate cleansing in the area between a user's adjacently located teeth.

Other prior art systems include rotating bristles which may be advantageous for application between teeth but are not as efficient for cleaning flat areas. In some cases, these types of systems may be abrasive to gum tissue.

Such prior art systems do not provide for the advantageous bristle rotation and oscillatory displacement in separate planes while simultaneously providing a pulsating stream and spray of cleansing liquid to remove contaminants and in which the overall system is self-refilling, wireless and tubeless.

Additionally, prior art systems do not provide for a stationary head housings allowing the bristles to be reciprocally and reversibly displaced which provides the user additional comfort during the brushing operation.

The disadvantages of the above-referenced prior art systems are overcome to some extent by toothbrush systems described in U.S. Pat. Nos. 5,301,381 and 5,321,866, and invented by the Applicant of the present Patent Application. Such systems include a handle member which defines an internal handle chamber for containment therein of a cleansing liquid container. In each of these prior art systems, the handle member is coupled to a head housing which has bristles extending from the housing. The bristles are displaceably oscillated about a central axis and simultaneously are rotated about an axis which extends in a perpendicular direction to the longitudinal direction and is further responsive to the oscillating displacement of the bristles. A mechanism is provided for delivering a liquid from the handle through the head member and external the toothbrush system adjacent the bristles. In this manner, there is provided a pulsating liquid flow from the toothbrush system with a combined rotation and oscillation of the toothbrush bristles in a plurality of planes.

Despite the advantages of the toothbrush systems described in '381 and '866 Patents, these prior toothbrushes do not have an irrigating member "feeling" the surface geometry found in the mouth of a user during the toothbrushing process which delivers the anti-microbial irrigant or other medicinal fluid directly into the space between the teeth once such a space is "found". Further, such prior toothbrush systems do not permit automatic convergence and/or divergence of the bristle tufts responsive to the teeth surface geometry for cleaning under the gum line or between the teeth. Thus, an even more sophisticated and unique toothbrush system, which dramatically increases the efficiency of plaque removal from the teeth, as well as between teeth and gums is needed in the art.

In typical toothbrush systems, toothbrush heads should be replaced every three months to maintain maximum cleaning efficiency. Since the average consumer does not generally keep track of the purchase date, they are not aware of the time in which the head unit should be replaced. To aid the consumer, some major toothbrush manufacturers have resorted to using dyed bristles that are supposed to indicate when the head should be replaced. As the brush gets older, the dye wears off starting at the tips of the bristles and wearing towards the bristle platform. The problem with this type of indicator is that the consumer can never quite tell when the head should be replaced. Thus, a definitive indicator, "telling" a user when to replace the head unit is needed in toothbrush systems of the current art.

SUMMARY OF THE INVENTION

It is an object of the present invention to provide a toothbrush system which includes a unique combination of mechanical brushing forces applied to the tooth surface as well as particular fluid dynamics for direct application of anti-microbial irrigant liquids directly into the spaces formed between the teeth in order to increase the efficiency of plaque removal from the teeth as well as from the space between the teeth and gums.

It is a further object of the present invention to provide a toothbrush system which permits three-dimensional cleaning of all surfaces of the teeth. Such a toothbrush system has a telescopic irrigation nozzle powered by the pulse of the anti-microbial irrigant which gives the toothbrush head the distinguishing ability to "feel" the contours of the teeth and to find the spaces therebetween. Once the irrigation nozzle "senses" the space between the teeth or any other concave area, it extends into the subject area, releases the anti-microbial irrigant, and retracts. The irrigation nozzle, in addition to delivery of the anti-microbial fluid directly into the space between the teeth additionally has a textured external surface which mechanically cleans between the teeth thus enhancing the cleaning process.

Another object of the present invention is to provide a toothbrush system having a hydraulically actuated/continuously variable telescoping bristle platform which negotiates the complex surface geometry found in a user's mouth. The subject system has a unique bristle configuration to permit the toothbrush head to automatically adjust the position of the bristle tops for cleaning under the gum line as well as between the teeth and on the surfaces of the teeth.

According to the teachings of the present invention a toothbrush system is provided which comprises a handle member defining an internal chamber therein containing a medicinal or cleansing fluid. A head member is secured to the handle member and a head unit is arranged at the end of the head member opposingly located with respect to the handle member. The head unit includes a bristle platform with bristles arranged on the bristle platform in circumferential disposition with respect to the central axis of the head unit. A hydraulically biased irrigating member is fluidly coupled to the internal chamber within the handle member through a fluid conduit extending through the head member of the toothbrush. The irrigating member includes an irrigator nozzle reciprocating along the central axis of the head unit between a retracted and extended position thereof. In the extended position, the irrigator nozzle releases the fluid into the mouth of a user.

The irrigator nozzle reciprocates along the central axis of the head unit responsive to the teeth surface geometry and the fluid is released through the irrigator nozzle once the irrigator nozzle "finds" the space between teeth and extends itself thereinto.

The bristle platform is capable of performing a diversity of motions while negotiating the complex surface and geometry found in the mouth. Such motions include reciprocation through an arc with respect to the central axis of the head unit, and/or angular oscillation as well as reciprocation along the central axis of the head unit. The bristles of the head unit have generally ovoidly shaped bristle tufts. This unique bristle configuration allows the toothbrush head to automatically adjust the position of the bristle tufts for cleaning under the gum line or between the teeth. This positioning is important since, depending on the direction of reciprocating of the bristles through an arc, the bristle tufts either converge (thus facilitating the cleaning the flat surfaces of the teeth and under the gum line) or diverge for facilitating cleaning between the teeth.

The head unit includes inner and outer bristle platforms which are capable of being telescopically displaced and/or of reciprocating through an arc each with respect to the other. The inner and outer bristle platforms are additionally capable of angular articulation each with respect to the other.

The irrigating member includes an elastic diaphragm, which may be a conical diaphragm, with the irrigating nozzle attached to the tip of the elastic diaphragm. The diaphragm has walls defining an internal diaphragm space therebetween and a central opening defined at the tip of the elastic diaphragm. The irrigating nozzle has a central channel formed therethrough terminating in a fluid egress port. The central opening of the elastic diaphragm is directly coupled to the fluid egress port through the central channel of the irrigating nozzle. Fluid is supplied in a pulsing mode to the internal diaphragm space and is contained therein, thus fluidly biasing the irrigating nozzle while in the retracting position. The fluid is released from the irrigating nozzle through the fluid egress port once the irrigating nozzle "finds" the space between teeth or any concave area and extends therein. The fluid is supplied from the internal chamber within the handle member in a pulsing manner.

The irrigating nozzle has an externally textured surface which facilitates cleaning between the teeth. In addition to the liquid egress port, the irrigating nozzle also includes relief ports formed therein through which the medicinal or anti-microbial fluid can release when the irrigator nozzle is in its retracted position.

The toothbrush system further includes a motor and a rotationally driven drive shaft connected to the motor. The drive shaft includes a cam pin positioned at one end thereof which is engaged in a cradle drive slot formed in the head unit. In this manner, engagement between the cam pin and the cradle drive slot generates reciprocation of the bristle platform through an arc in counter-clockwise and clockwise directions. During the negotiation of the bristle platform along the surface of the teeth, the clockwise and counter-clockwise reciprocation of the bristle platform through an arc results in the ovoidly configured bristle tufts either to converging or diverging in order that substantially all surfaces of the teeth, between the teeth, and under the gum line may be cleaned. This automatic adjustment of the bristle direction, in combination with irrigation of all surfaces of the teeth and spaces between the teeth with anti-microbial or any other fluid involved in the treatment of the teeth, provides for an effective teeth cleaning process.

The toothbrush system of the present invention includes a wear indicating unit which may be designed in a number of modes. In one implementation, the wear indicating unit includes a red colored coating deposited around the drive shaft at a predetermined location, a blue colored coating deposited on top of the red coating, an abrasive wear pad embedded into the head member in close proximity to the blue coating and in engagement therewith, and an indicator window formed through a wall of the head member in alignment with the blue and red coatings to expose portions thereof therethrough. When the blue coating has been worn by the abrasive wear pad during rotation of the drive shaft, the red coating is exposed through the indicator window thus indicating the need for replacement of the toothbrush.

In another implementation of the wear indicating unit, the shaft may be formed of a conductive material with an insulating coating deposited thereon. The brush head has an abrasive material positioned in engagement with the insulating coating. When the insulating coating wears off because of its contact with abrasive material an electrical "closed circuit" occurs lighting an LED indicative of the need to replace the toothbrush.

Still in another embodiment, the wear indicating unit may include a metal spike positioned on the head member in engagement with the drive shaft (in this embodiment the drive shaft may be formed of plastic). The metal spike, during a rotation of the drive shaft cuts the shaft, thus causing the failure forcing replacement of the toothbrush.

These and other novel features and advantages of the subject invention will be more fully understood from the following detailed description of the accompanying drawings.

BRIEF DESCRIPTION OF THE DRAWINGS

FIGS. 8A and 8B, respectively, illustrate schematically how the telescopic irrigation nozzle "feels" the contour of the teeth, and "finds" the space between the teeth (FIG. 8B);

FIG. 10 shows one embodiment of the wear indicator of the toothbrush of the present invention; and, FIGS. 11 and 12 illustrate alternative embodiments of the wear indicator of the toothbrush of the present invention.

DESCRIPTION OF THE PREFERRED EMBODIMENTS

Figure 1:
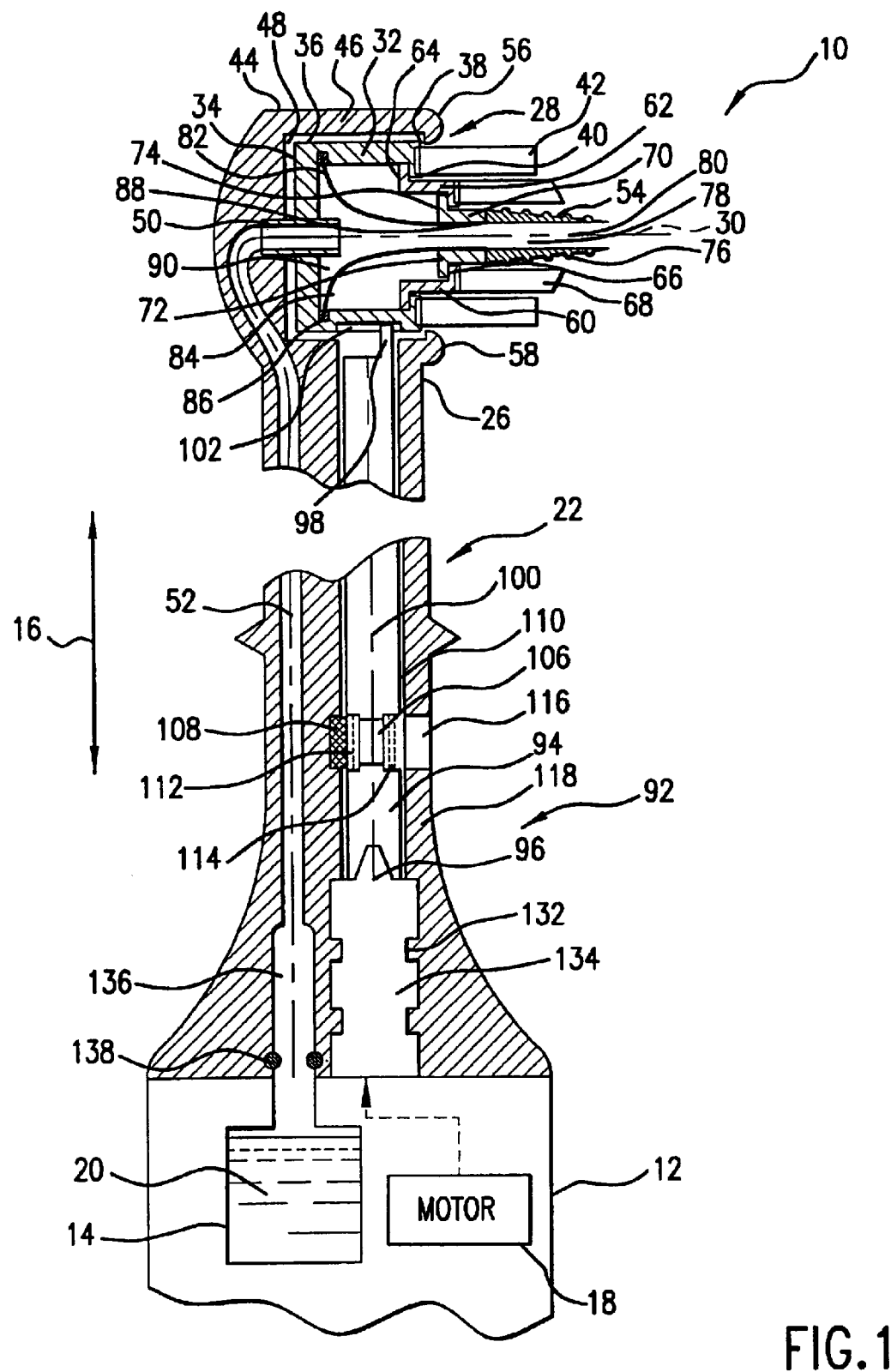
FIG. 1 is a longitudinal cross-section of the side view of the toothbrush of the present invention.
Figure 2:
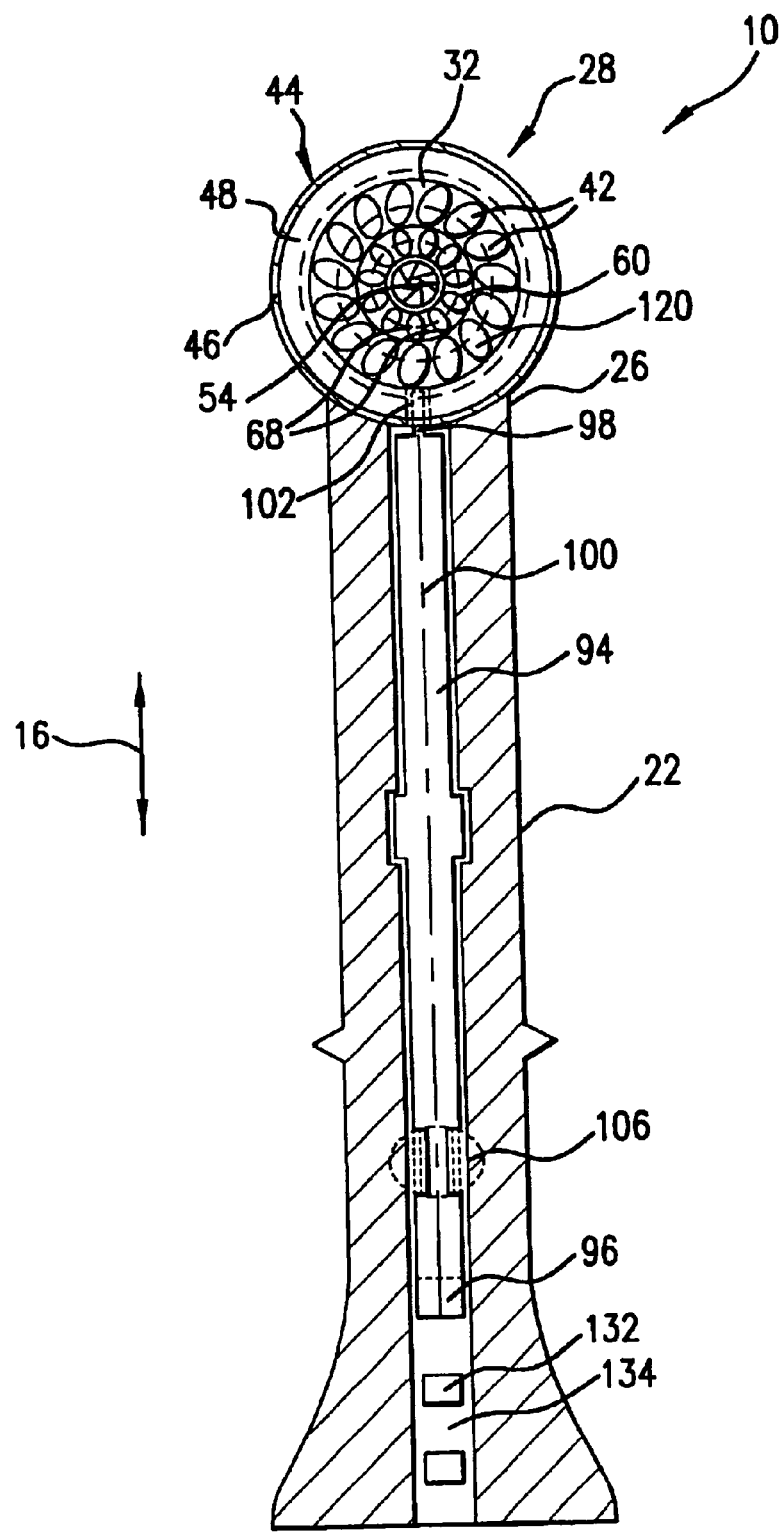
FIG. 2 is a longitudinal cross-section of a front view of the present invention.

Referring to FIGS. 1 and 2, there is shown a toothbrush system 10 designed for highly effective removal of contaminants from the teeth and gums of a user. The system 10 provides a user with the maximization of bristle/tooth interface while simultaneously providing anti-microbial fluid force to remove unwanted contaminants not only from the exposed surfaces of the teeth but also in spaces therebetween.

In particular, toothbrush system 10 includes a handle member 12 having an internal handle chamber 14. As can be seen, handle member 12 extends in longitudinal direction 16 as defined by the directional arrows shown in FIGS. 1 and 2. The handle member 12 may be formed of one piece or multi-piece molded plastic or some like material, not important to the inventive concept as herein described with the exception that it have a diameter which allows a user to easily hold toothbrush system 10 in one hand during the normal brushing operation and further that it is capable of accepting the structural loads imposed thereon. The handle member 12 may include a standard commercially available two pole on/off switch (not shown in the Drawings) for activating a motor 18 responsive to electrical input from standard batteries or other power source (not shown in the Drawings). The handle 12 further includes a push button valve to control a flow of fluid 20 contained in the internal chamber 14. Such electrical switches and valves are well-known in the prior art and are not part of the invention concept as herein described.

A head member 22 extends in longitudinal direction 16 and defines a head housing 24 at one end 26 of which a head unit 28 is secured. The head unit 28 has a central axis 30. The head unit 28 includes a diaphragm cradle 32 having a bottom section 34. Cylindrically shaped walls 36 join at one edge thereof to the peripheral bottom 34. Another end 38 includes a cradle platform 40 to which outer bristle tufts 42 are secured. The diaphragm cradle 32 is rotationally secured within a head housing 44 positioned at the end 26 of the head member 22.

The head housing 44 includes walls 46 defining a chamber 48 at the bottom of which a fluid conduit tube 50 is located which serves as the rotation axis of the diaphragm cradle 32 and further provides fluid communication between a fluid conduit 52 and the irrigating nozzle 54 as will be described in further paragraphs.

At the edge 56 of the walls 46 of the head housing 44 there is provided a cradle retainer 58 extending around the periphery of the head housing 44. The diaphragm cradle 32 within the head housing 44 is rotatably secured onto the fluid conduit tube 50 and is maintained in cooperation with the chamber 48 of the head housing 44 by a cradle retainer 58. The cradle retainer 58 engages the cradle platform 40 thus retaining the diaphragm cradle 32 within the head housing 44.

The head unit 28 further includes a telescopic inner bristle platform 60 which has cylindrically shaped walls 52 with lower and upper rims 64 and 66 extending at both edges of the walls 62 of the inner bristle platform 60 along the periphery thereof. The rim 64, as best shown in FIG. 1, engages the cradle platform 40 of the diaphragm cradle 32 when the inner bristle platform 60 is in its extended position, in order to keep the inner bristle platform 60 from being displaced from the head housing 44. The rim 66 has bristle tufts 68 attached thereto which are generally ovoid in cross-section as will be described in further paragraphs.

A telescopic nozzle platform 70 is telescopically secured within the inner bristle platform 60. The telescopic nozzle platform 70 includes a cylindrically shaped body 72 and a rim 74 extending along the periphery of the cylindrically shaped body 72 and which maintains the telescopic nozzle platform 70 within the inner bristle platform 60 when the telescopic nozzle platform 70 is in its extended position. This is accomplished by the engagement of the rim 74 and the rim 66 of the inner bristle platform 60. The irrigating nozzle 54 is secured to the cylindrically shaped body 72 of the telescopic nozzle platform 70. The irrigating nozzle 54 includes an externally textured outer surface 76, a central channel 78, and a fluid egress port 80.

Within the head unit 28 is provided an elastic (rubber) diaphragm 82 which is secured at the edge 84 thereof within the diaphragm retainer 86 extending at the periphery of the bottom 34 of the diaphragm cradle 32. The diaphragm 82 at an opposite edge 88 (when taken with respect to edge 84) is secured within the cylindrically shaped body 72 of the telescopic nozzle platform 70. The diaphragm 82 forms a central channel within the cylindrically shaped body 72 which is in fluid communication with the central channel 78 of the irrigating nozzle 54.

As shown in FIG. 1, the inner bristle platform 60 and the telescopic nozzle platform 70 may freely reciprocate along the central axis 30 of the head unit 28. FIGS. 7A, 7B, 8A, and 8B, show the irrigating nozzle, as well as inner bristle platform 60, either in their retracted position (FIGS. 7A and 8A), or in their extended position (FIGS. 1, 6, 7B, and 8B).

As best shown in FIG. 1, the fluid conduit 52 extends through the head member 22 for coupling the internal chamber 34 with the fluid conduit tube 50 for pulsed delivery of the fluid 20 into the chamber 90 formed by the walls of the diaphragm 82.

It is understood that in a manner similar to the handle member 12, the head member 22 and the head housing 44 may be formed of a plastic type composition and may be molded in one or multi-piece formation. Toothbrush system 10 includes a liquid delivery mechanism which may be similar to that provided and described in prior art U.S. Pat. Nos. 5,301,382 and 5,321,866. The liquid delivery mechanism may, as an example, include a piston member or other type of flow mechanism to provide liquid flow which may be drawn in a pulsating manner through the fluid conduit 52 into the chamber 90 defined within the diaphragm 82.

The liquid delivery mechanism may further include a first liquid conduit which is in fluid communication with the liquid container 14. Another liquid conduit may be used which is in fluid communication with the head unit flow passageway 50. A standard one-way valve may be mounted on the first liquid conduit. In this manner, cleansing liquid may be dispensed from the liquid container 14 through the first liquid conduit and then through the one-way valve member. The one-way valve member insures that cleansing liquid will not be passed in a reverse manner into the first liquid conduit.

Liquid delivery mechanism further may include a mechanism for actuating the one-way valve member. There may be provided a linearly and reversibly displaceable piston member which is coupled to the overall drive mechanism of the toothbrush and which is displaceable within piston chamber. The piston chamber is in fluid communication with the second liquid conduit and one-way valve member. During operation of the toothbrush, its drive mechanism creates a pressure differential between the piston chamber and first liquid conduits to allow liquid to flow from first liquid conduit in the system chamber and then subsequently into second liquid conduits for dispensation through head flow passageway 50. As the piston member moves in a radial direction towards an outer wall of the handle member 12, liquid contained within the piston chamber is forced into second liquid conduit but is blocked from passage into first liquid conduit by one-way valve member. There may also be included a secondary one-way valve which is mounted at the entrance of the second liquid conduit to prevent backflow of fluid and air into the piston chamber. Thus, when a low pressure is provided in the piston chamber, fluid will not pass thereto from the second liquid conduit.

As piston member is linearly displaced within piston chamber in a direction towards the central axis of the handle member, a lower pressure is obtained within piston chamber which closes the secondary valve and opens one-way first valve member and allows cleansing fluid to be dispensed therein. As the piston moves reversibly in a linear direction within piston chamber, a pulsating liquid flow is provided through a second liquid conduit. As the piston moves radially outward, the fluid within the chamber is compressed and a resulting high pressure ensured. Fluid is then passed into the second conduit with no flow into the first liquid conduit due to the action of one-way valve. This pulsating flow of clean liquid eventually egresses into the chamber 90 formed by the walls of the diaphragm 82.

Figure 4:
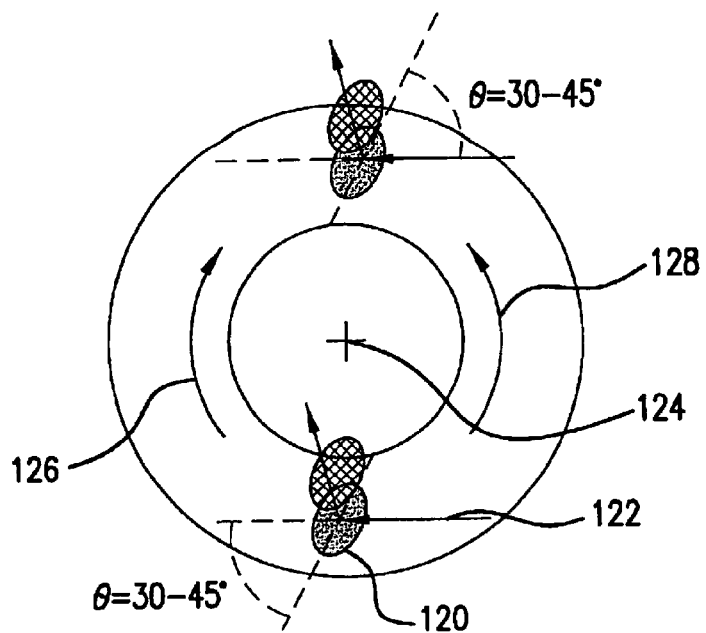
FIG. 4 is a schematic illustration of the effects of the force vectors acting upon the individual ovoid bristle tufts when the bristle platform reciprocates through an arc.
Figure 5:
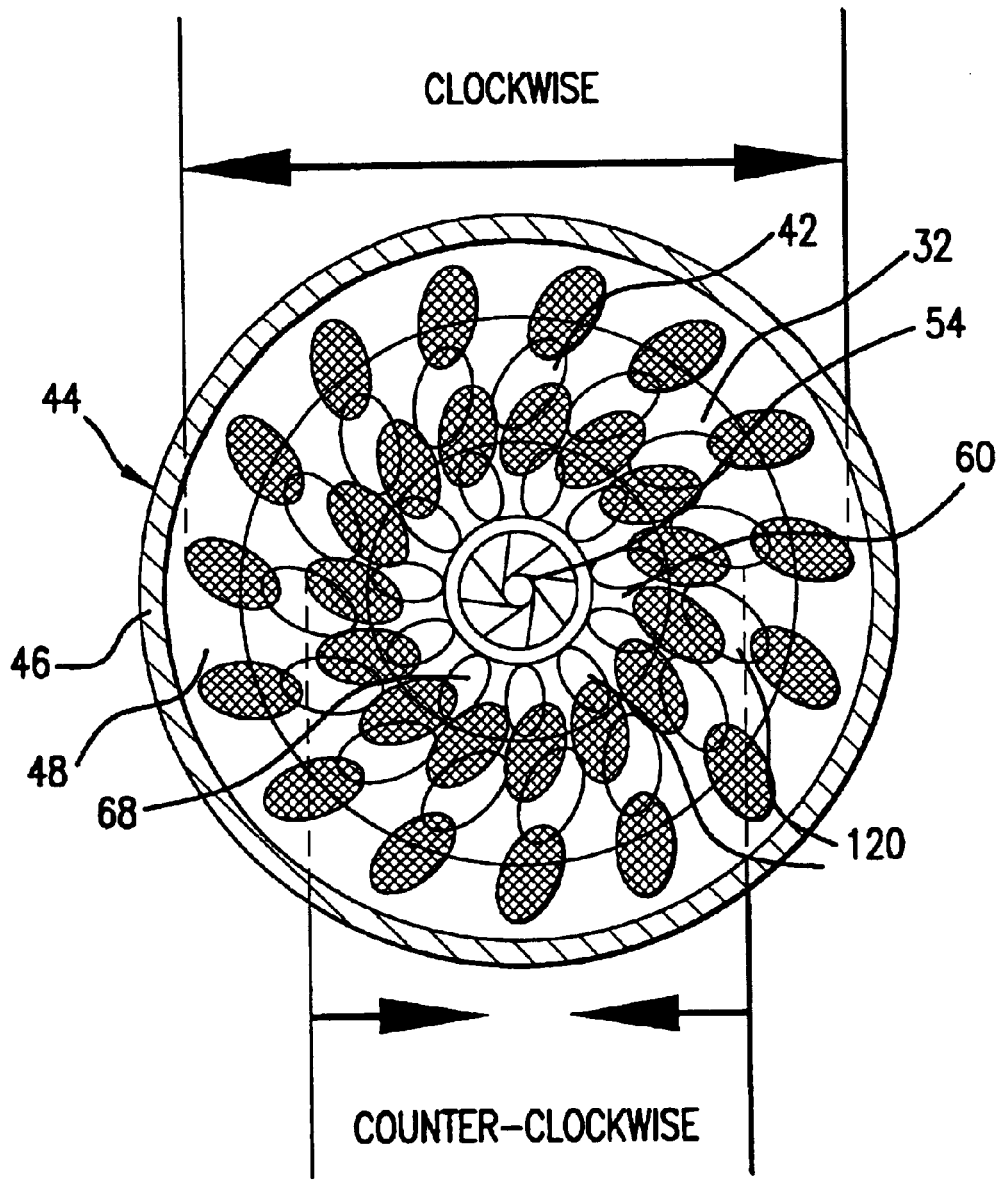
FIG. 5 is a front view of the bristle platform of the head unit of the present invention demonstrating the net effect of bristle platform reciprocation in clockwise and counter-clockwise directions.

The toothbrush system 10 of the present invention further includes a drive mechanism 92 which includes a drive shaft 94 rotationally activated by the motor 18. The drive shaft 94 extends within the head member 22 and includes at one end thereof a drive shaft coupling 96 and further having at another end a drive shaft cam pin 98 which extends off-axis from the central axis 100 of the drive shaft 94. The cam pin 98 engages a molded cradle drive slot 102 formed at the walls of the diaphragm cradle 32. When the drive shaft 94 is rotated with respect to central axis 100, the cam pin 98 is displaced within the slot 102 and results in reciprocation of the diaphragm cradle 32 through an arc in a clockwise or a counter-clockwise direction as shown in FIGS. 4 and 5 of the Drawings.

Figure 6:
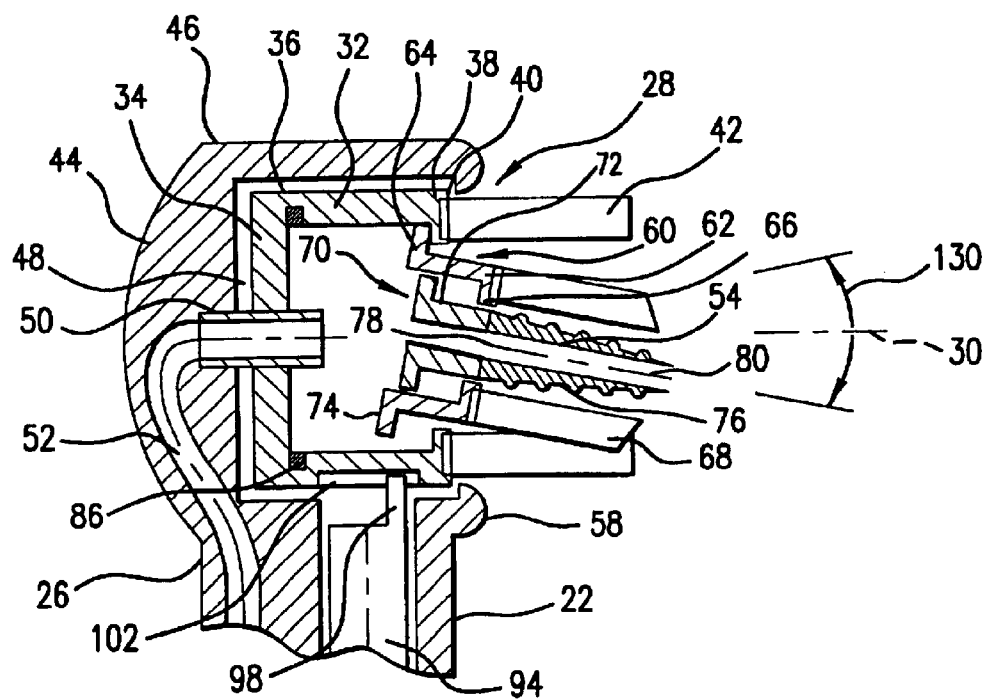
FIG. 6 is a central cross-section of the head unit of the toothbrush of the present invention illustrating the angular articulation capability of the bristle platform.

The inner bristle platform 60 is keyed to the diaphragm cradle 32 and therefore performs reciprocating motions through an arc therealong. However, the keyed arrangement between the diaphragm cradle 32 and the inner bristle platform 60 permits a certain degree of freedom therebetween so that the inner bristle platform 60 is free to perform angular articulation with regard to the diaphragm cradle 32 as best shown in FIG. 6 and as will be described in following paragraphs herein. The key arrangement between the diaphragm cradle 32 and inner bristle platform 60 may include a slot-notch arrangement, well known to those skilled in the art and is thus not described herein in detail.

Further, as shown in FIGS. 1, 2, and 10–12, the toothbrush system of the present invention includes a wear indicator 106 which will be further described in detail, and which is envisioned in three alternative embodiments of the toothbrush system 10. The wear indicator 106 is a unique toothbrush head replacement indicator, which will indicate to a user of the toothbrush system 10 when it is time to replace the head unit 28 with a new one. The wear indicator 106 is a definitive unit which precisely "tells" to a user when to replace the head unit.

The wear indicator, as shown in FIG. 10, includes an abrasive wear pad 108 arranged at the drive shaft channel 110 in close proximity to the drive shaft 94, a red or other color coating 112 embracing the drive shaft 94 at a predetermined location thereof in alignment with the abrasive wear pad 108, and a blue or other color coating 114 deposited on the top of the red coating 112 in contiguous engagement with the abrasive wear pad 108. The wear indicator 106 also includes an indicator window 116 formed in the wall 118 of the head member 22 through which the coating is exposed, in order that the user can clearly visualize the color of the coating exposed. It is to be understood that reference to "red" and "blue" coating colors are merely representations of any different colored coatings.

In operation, as the drive shaft 94 performs a continuous 360° rotation, the abrasive wear pad 108, being in contiguous contact with the blue coating 114, removes the blue coating 114 and exposes the red coating 112 indicating that the head unit 28 needs replacement. The blue coating 114 and the wear pad 108 are designed to allow the user approximately 180 uses (each of 2 minutes duration) before the red coating is exposed. The red coating 112 may contain a substance that becomes "sticky" when in contact with the abrasive wear pad 108. The extra friction thus created would result in an increased current draw on the motor 18 and will trip the motor protection circuit (not shown in the Drawings), thus forcing the user to replace the head unit 28.

The significance of the contrasting colors is particularly pointed out by a mnemonic device which aids the user in remembering replacement times. In effect, "When the Dot is Blue, the Brush is New, When the Dot Turns Red, Replace the Head"™.

In another embodiment of the wear indicator 106 shown schematically in FIG. 11, the drive shaft 94 may be formed of an electric conductive metal with an insulating coating 107 instead of a blue or other colored coating 114. The abrasive wear pad 108 may be replaced with an electric motor "brush" 109 that contains an abrasive material. The electric motor "brush" 109 wears through the insulating coating 107 thus creating a closed circuit when it contacts the drive shaft 94. In this embodiment, the wear indicator 106 also includes an indicating device 111, such as LED located on the toothbrush body for generating a light beam whenever the closed circuit is created. A switch may be provided (not shown in the Drawings) which will open the motor circuit in response to creating a closed circuit whenever the abrasive materials wears through the insulating coating 107 thereby disabling the toothbrush 10.

Figure 12:
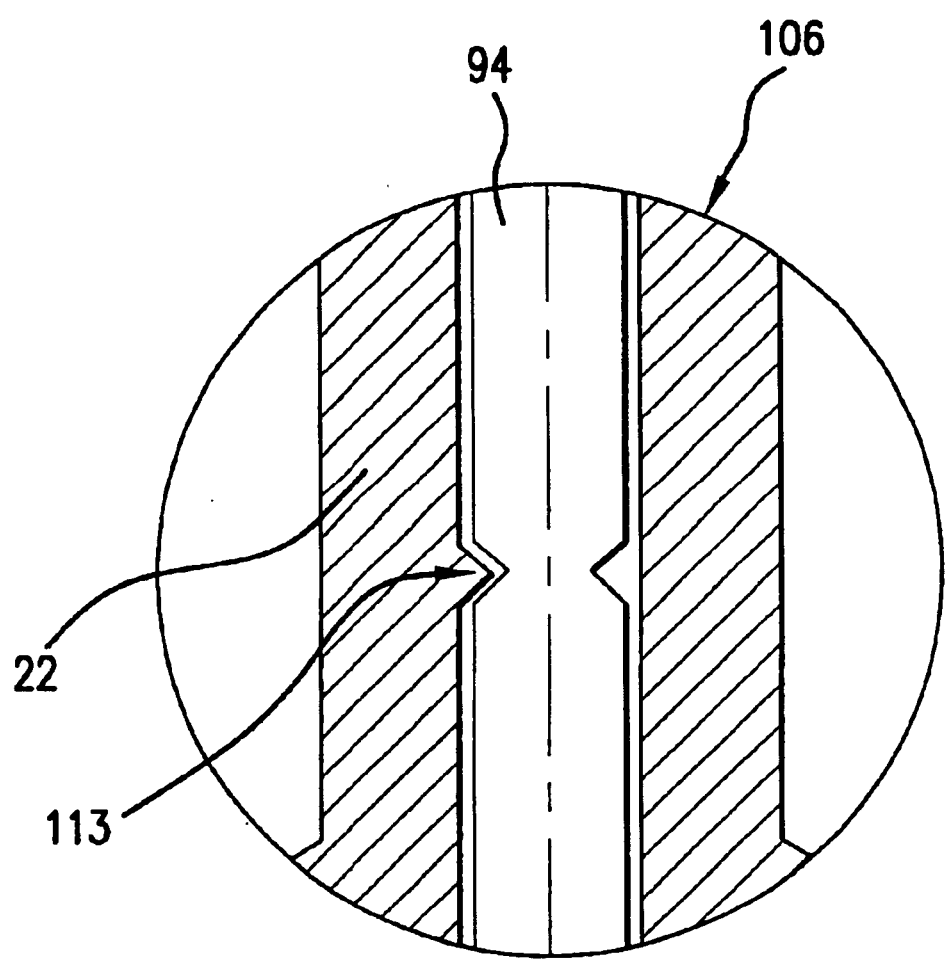

In still another embodiment of the wear indicator 106 shown in FIG. 12, the drive shaft 94 can be formed of plastic, and the wear pad 108 shown in FIG. 10, may be replaced with a metal "spike" 113 which during the drive shaft 94 rotation would eventually cut the plastic drive shaft 94 at a predetermined rate. When the torque placed on the drive shaft 94 by the motor 18 exceeds the physical characteristics of the thinning drive shaft 94 the shaft 94 breaks, thus disabling the toothbrush 10 and requiring replacement of the head unit 28.

Figure 3:
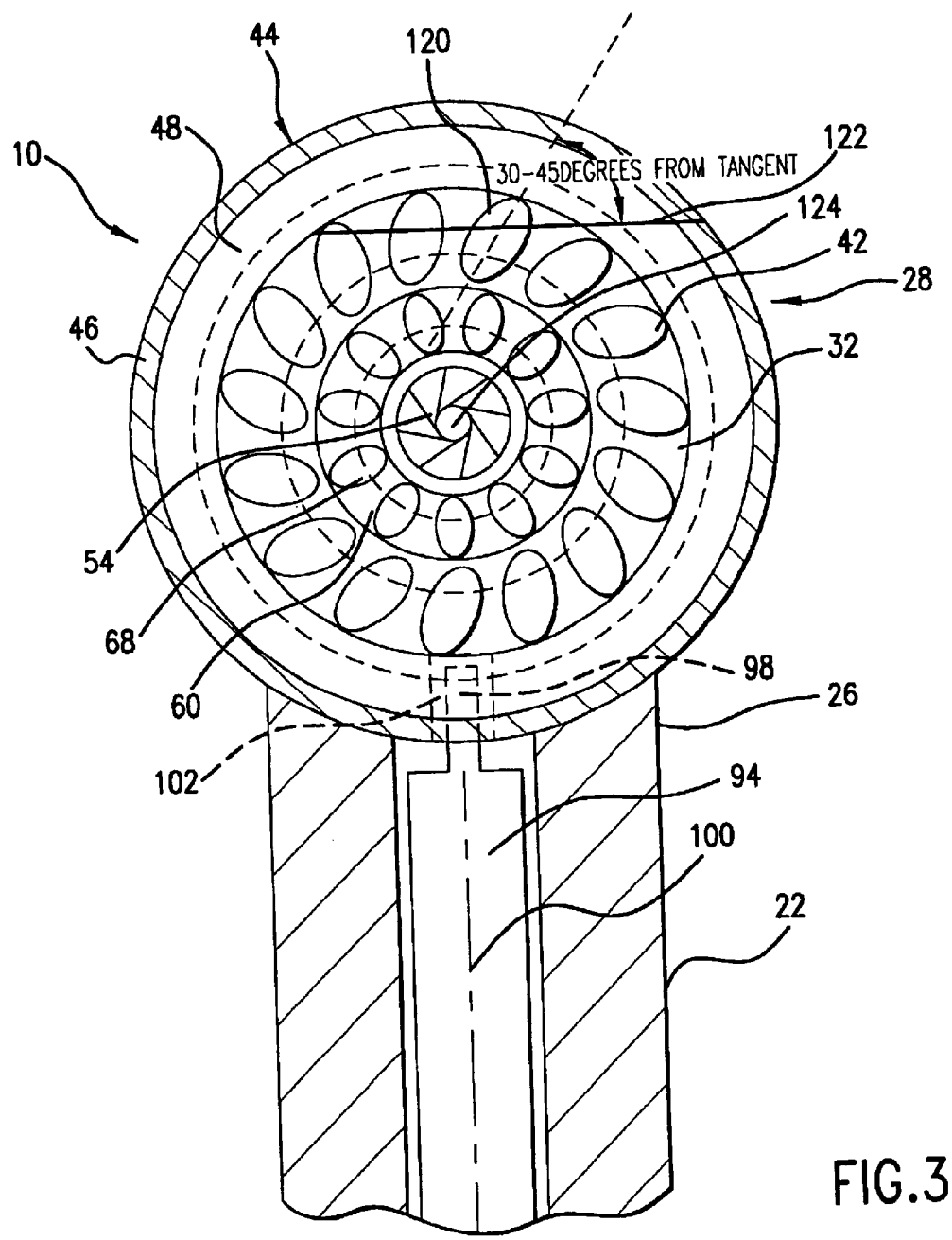
FIG. 3 is a front view of the bristle platform of the head unit of the present invention.

As shown in FIGS. 2, 3, 4, and 5, the bristle tufts (inner bristles 68 as well as outer bristle tufts 48) are formed in a generally ovoid shape. As shown in FIGS. 3 and 4, the long axis of each oval 120 is positioned at a 35–45° angle to a line 122 drawn as a tangent to the cradle platform 40. Such an ovoid tuft configuration, combined with the angulated long axis position of each oval 120 allows the bristle tufts to be displaced towards or away from the platform center 124 relative to the vectors of force acting upon the bristle tufts with respect to the rotational direction of the cradle platform 40 and the inner bristle platform 60.

FIG. 4 illustrates the effects of the vectors 126 of force acting upon the individual ovoid bristle tufts. Either outer tufts 42, or inner tufts 68, the inner bristle platform or the diaphragm cradle reciprocate through an arc of approximately 60° around the central axis 124 (altogether 120° in both directions). The curved directional arrow 126 shows the outward displacement in the clockwise rotation and the curved directional arrow 128 shows the inward displacement of the bristle tufts while the respective bristle platform rotates in counter-clockwise direction.

FIG. 5 demonstrates the net effect of bristle platform reciprocation upon the positioning of the ovoid bristle tufts relative to the central axis 124 in the clockwise rotation. The ovoid bristle tufts are forced away from the central axis 124, thus effectively widening the reach of the outer bristle tufts 42. This is important when attempting to remove plaque below the gum line. While in the counter-clockwise rotation, the ovoid bristle tufts are forced towards the central axis 124, thus effectively moving the oval bristle tufts inward towards the central axis 124. This is an important consideration when removing plaque between the teeth.

FIG. 6 illustrates the angular articulation capability of the bristle platform. Angular articulation enhances the performance of the toothbrush head in hard-to-reach areas of the mouth where the inner bristle platform 60 can angularly articulate with respect to the central axis of the head unit 28. As described in previous paragraphs, the inner bristle platform 60 is generally keyed to the diaphragm cradle 32 in order to follow the rotational motion of the diaphragm cradle 32 caused by the cam pin 98 engaging the cradle drive slot 102 during the drive shaft 360° continuous rotation.

However, despite of being keyed to the diaphragm cradle 32, the inner bristle platform 60 nevertheless is provided with a predetermined degree of freedom displacement in order that the inner bristle platform 60 may articulate independently from the diaphragm cradle 32 as shown in FIG. 6, in a predetermined angular sector 130. As shown, the telescopic nozzle platform 70 positioned within the inner bristle platform 60, articulates in the angular sector 130 along with the inner bristle platform 60 to thus enhance the capability of the irrigating nozzle to reach the hard-to-reach areas of the mouth.

The key arrangement between the diaphragm cradle 32 and the inner bristle platform 60 may be implemented as a slot-notch arrangement, well known to those skilled in the art. Such a key arrangement provides "dependence" between the platforms during rotational displacement thereof. Simultaneously, such a key arrangement provides "independence" of the inner bristle platform from the diaphragm cradle for the angular articulation, shown in FIG. 6.

In operation, a user of the toothbrush system 10 of the present invention, turns "ON" the system thus activating the motor 18 and initiating the 360° continuous rotation of the drive shaft 94. The drive shaft 94 is coupled to the motor 18 through the system of the drive shaft coupling 96 engaging the drive shaft 94. The drive shaft coupling 96 is secured within the head member 22 by the drive shaft coupling retainer 132 inserted into the head member 22 through the drive shaft coupling opening 134 formed on the end of the head member 22 engaging the handle member 12. The 360° continuous rotation of the drive shaft 94 results in a responsive 360° continuous rotation of the cam pin 98. The cam pin 98 being engaged in the cradle drive slot 102, formed in the wall of the diaphragm cradle 32, results in a reciprocation of the cradle 32 through an arc in both clockwise and counter-clockwise directions.

Simultaneously, irrigating fluid contained in the internal chamber 14 defined within the handle member 12, is supplied in a pulsing mode into the fluid conduit 52 through the fluid coupling port 136. In order to seal the connection between the internal chamber 18 and the conduit 52, a fluid coupling "O" ring 138 is positioned at the entrance of the fluid coupling port 136. The irrigating fluid thus is supplied through the fluid conduit tube 50 into the chamber 90 formed by the walls of the diaphragm 82, then fills the chamber 90 and the central channel 78. The irrigating nozzle 54 has a positive fluid bias while in the extended position.

Figure 7A:
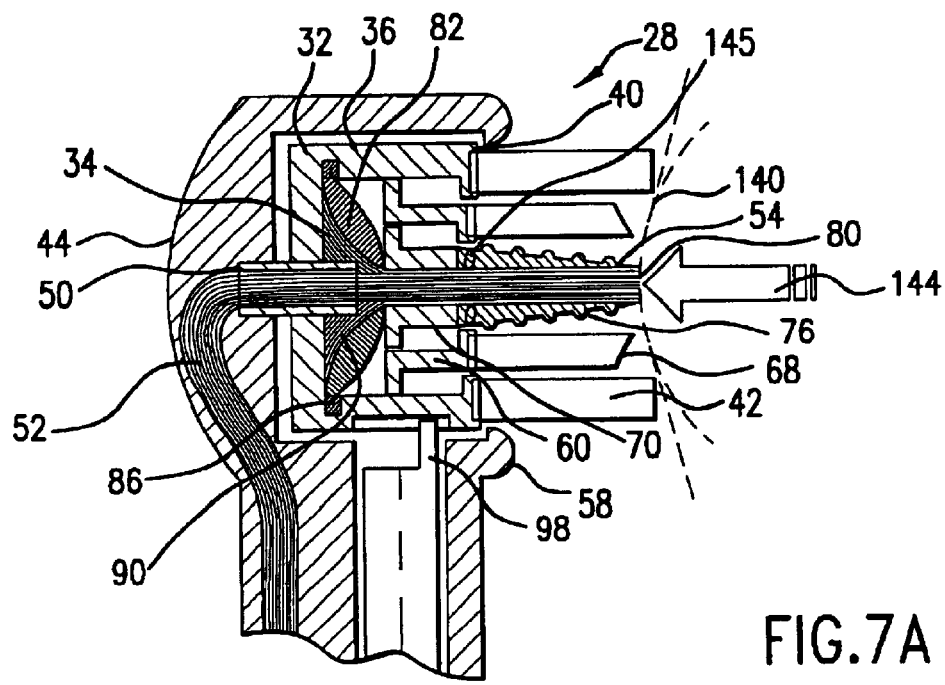
FIG. 7A shows the cross-section of the head unit of the present invention with the irrigation nozzle in its retracted position.
Figure 7B:
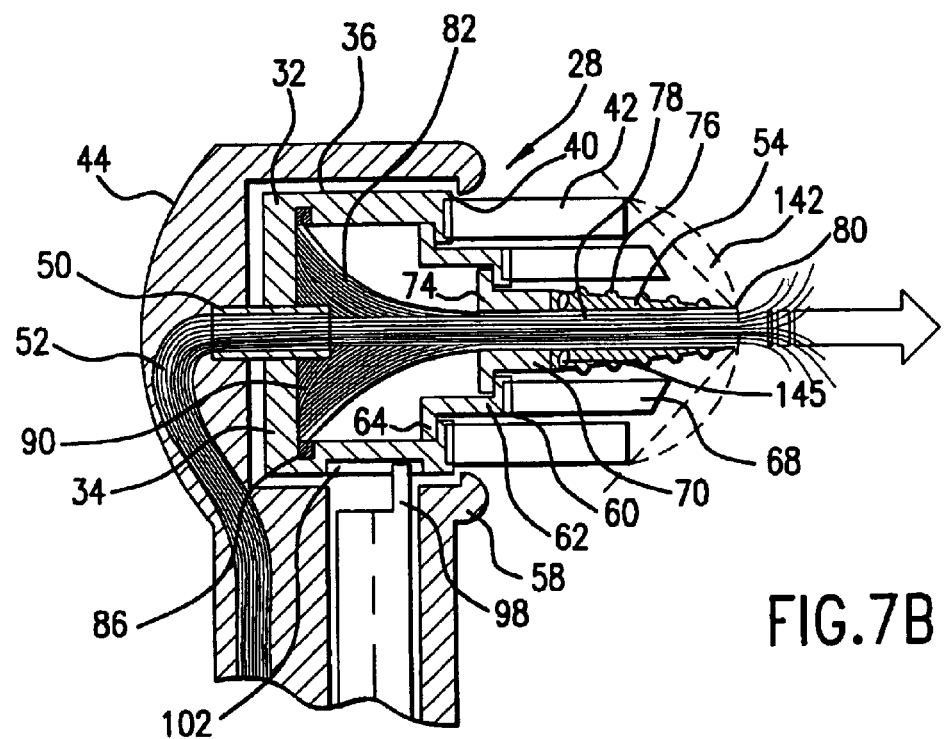
FIG. 7B shows the cross-section view of the head unit of the present invention with the irrigation nozzle in its extended position.

As shown in FIGS. 7A and 7B, which demonstrates the ability of the toothbrush system 10 of the present invention to negotiate the complex geometry of the teeth and gums, when a user moves the toothbrush around a convex surface 140 of the teeth, the irrigating nozzle 54, as well as the telescopic nozzle platform 70, along with the inner bristle platform 60, are all in the retracted position; and no fluid is released from the irrigating nozzle 54 through the fluid egress port 80.

However, as shown in FIG. 7B, as the bristle platform 60 is maneuvered within the concave area 142, the pressure force 144 retaining the irrigating nozzle 54 in its retracting position ceases, and the diaphragm 82 being fluidly biased positively and is pushed to the extended position thereof (FIG. 7B) along with the inner bristle platform 60 and the telescopic nozzle platform 70. In the extended position, the fluid is no longer captured within the chamber 90 and the central channel 78 and is free to be released therefrom. The fluid is then directly delivered to the concave area 142 such as the space between the teeth.

As shown in FIG. 7A, the irrigating nozzle 54 has fluid ports 145 formed therein. A small amount of the cleansing liquid is released therethrough when the diaphragm 82 is in its retracted position. The fluid is released through the ports 145 due to the fluid pressure created within the chamber 90 of the biased diaphragm 82. This fluid is supplied to the convex surfaces of the teeth to facilitate the cleaning process of such surfaces.

As shown in FIGS. 8A and 8B, while the toothbrush head 28 is moved along the teeth, from the position shown in FIG. 8A to FIG. 8B, the telescopic irrigation nozzle 54, "powered by the pulse" of the anti-microbial irrigant, "feels" the contour of the teeth and "finds" the spaces between them where plaque is deposited. Once the head unit 28 locates such a space, the telescopic irrigating nozzle 54 extends into the area and the fluid egress port 80 releases the fluid. The telescopic irrigating nozzle 54 has the textured surface 76 that facilitates a mechanical removal of plaque while the anti-microbial irrigant kills the bacteria associated with bad breath and gum disease.

Figure 9:
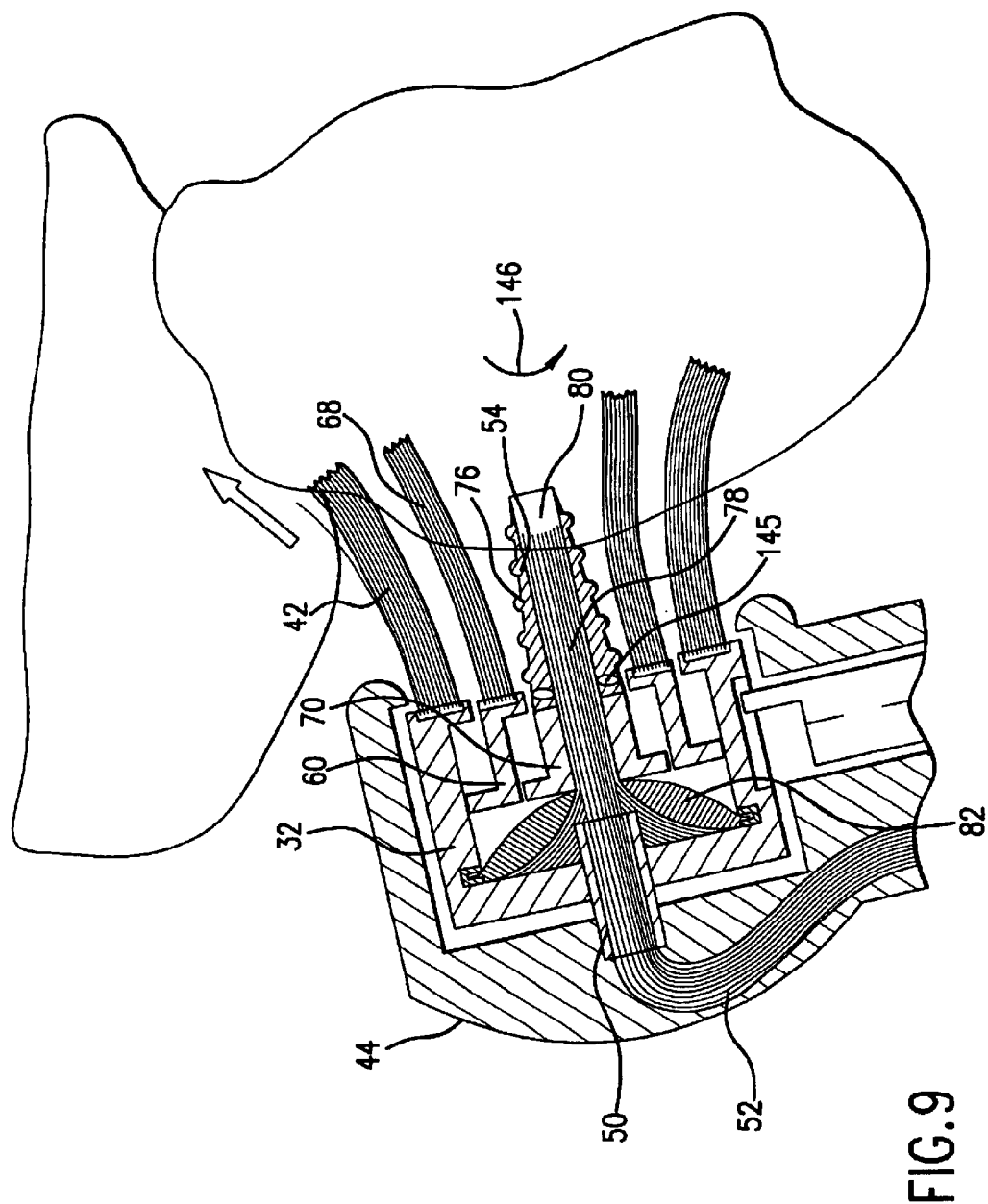
FIG. 9 is a representation of the head unit of the present invention rotating in clockwise direction, wherein the bristle tufts diverge away from the central axis of the head unit (for cleaning under the gum line), and wherein the irrigation nozzle is in its retracted position when the convex tooth anatomy is "sensed"

During negotiation of the head unit 28 along the teeth, the inner bristle platform 60 along with the diaphragm cradle 32, reciprocates arcuately in a clockwise or counter-clockwise direction. As an example, FIG. 9, shows the toothbrush head unit 28 rotating in clockwise direction 146. In this FIG. 9 depiction, the outer bristle tufts 42 are angled away from the central axis (as was described in previous paragraphs). The diaphragm 82 is in the retracted (or rest) position. In this geometry, the bristle tufts are capable of sweeping under the gum line and reacting to the convex tooth anatomy. If, however, as shown in FIG. 8B, the head unit 28 is rotated in counter-clockwise direction, and the space between the teeth is "found", the bristle tufts 42 and 68 are angled towards the central axis of the head unit with the diaphragm 82 is in its extended position in order that the outer and inner bristle tufts clean between the teeth and the cleansing fluid is delivered directly to the space between the teeth.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A toothbrush system for cleansing tooth surfaces and under a user's gum line, comprising:

(a) a handle member having an internal chamber containing a fluid;

(b) a head member secured to said handle member, a fluid conduit extending within said head member in fluid communication with said internal chamber of said handle member;

(c) a head unit secured to an end of said head member located remote from said handle member, said head unit having a central axis, said head unit including;

at least one bristle platform, bristles located on said at least one bristle platform in circumferential disposition with said central axis of said head unit, and a hydraulically biased irrigating member in fluid communication with said internal chamber of said handle member through said fluid conduit, said irrigating member having an irrigator nozzle reversibly reciprocatable along said central axis of said head unit between a retracted and an extended position of said irrigator nozzle, said irrigator nozzle releasing said fluid when said irrigator nozzle is in said extended position.

2. The toothbrush system of claim 1, wherein said irrigator nozzle reciprocates along said central axis of said head unit responsive to tooth surface geometry wherein said fluid is released through said irrigator nozzle subsequent to said irrigator nozzle having been extended into a space between teeth.

3. The toothbrush system of claim 1, further comprising a bristle driving mechanism operatively coupled to said head unit for reciprocating said bristles through an arc with respect to said central axis of said head unit.

4. The toothbrush system of claim 1, further comprising a bristle articulation mechanism for providing angular articulation of said at least one bristle platform with respect to said central axis of said head unit.

5. The toothbrush system of claim 1, further comprising a linear bristle driving mechanism for reciprocating said bristles along said central axis of said head unit.

6. The toothbrush system of claim 1, wherein said bristles include bristle tufts having an ovoid contour in cross-section, and wherein the long axis of each ovoid is at an angle 35°–45° with respect to tangent line drawn to said at least one bristle platform.

7. The toothbrush system of claim 1, wherein said at least one bristle platform reciprocates through an arc in a clockwise and counter-clockwise direction.

8. The toothbrush system of claim 7, including an inner bristle platform and an outer bristle platform, said inner and outer bristle platforms reciprocating through an arc in dependence each with the other.

9. The toothbrush system of claim 8, wherein said inner and outer bristle platforms are positioned in telescopic disposition each with respect to the other.

10. The toothbrush system of claim 8, wherein said inner and outer bristle platforms angularly articulate one with respect to the other.

11. The toothbrush system of claim 1, wherein said irrigating member includes an elastic diaphragm, said irrigator nozzle being attached to an end of said elastic diaphragm, said elastic diaphragm having walls defining an internal diaphragm space therebetween, a central opening formed at said end of said elastic diaphragm, said irrigator nozzle having a central channel formed therethrough and terminating in a fluid egress port, said central opening of said elastic diaphragm being in fluid communication with said fluid egress port through said central channel of said irrigator nozzle.

12. The toothbrush system of claim 11, wherein said fluid conduit is in fluid communication with said internal diaphragm space.

13. The toothbrush system of claim 1, wherein said irrigator nozzle has an externally textured surface for abrasively contacting a surface of said teeth.

14. The toothbrush system of claim 1, further including a fluid supply mechanism for supplying said fluid from said internal chamber to said irrigating member in a pulsing fashion.

15. The toothbrush system of claim 1, further comprising a motor and a drive shaft operatively connected to said motor for being rotated by said motor.

16. The toothbrush system of claim 15, wherein said drive shaft further includes a cam pin positioned at an end thereof, said at least one bristle platform of head unit having a cradle drive slot formed therein, said cam pin engaging said cradle drive slot and causing said at least one bristle platform to reciprocate through an arc once said drive shaft have been actuated by said motor.

17. The toothbrush system of claim 15, further comprising a wear indicator unit to indicate when said head unit is to be replaced.

18. The toothbrush system of claim 17, wherein said wear indicator unit includes a first coating deposited around said drive shaft at a predetermined location thereof, a second coating deposited on the top of said first coating, said second coating being distinct from said first coating, an abrasive wear pad embedded into said head member in contiguous engagement with said second coating, and an indicator window formed through a wall of said head member in alignment with said first and second coatings, when said second coating has been worn by said abrasive wear pad, said first coating is exposed through said indicator window, thus indicating the need for replacement of said head unit.

19. The toothbrush system of claim 17, wherein said drive shaft is made of a conductive material, said wear indicator unit comprising:

an insulating coating formed on said drive shaft at a predetermined position thereof, a brush operatively coupled to said motor, said brush having an abrasive material in engagement with said insulating coating, and indicating means, when said insulating coating has been removed by said abrasive material of said brush, said indicating means generating an indicia of the need for said head unit replacement.

20. The toothbrush system of claim 17, wherein said drive shaft is made of a plastic material, said wear indicator unit comprising:

a metal spike positioned on said head member in engagement with said drive shaft, said metal spike cutting said shaft during the rotating motion thereof causing failure of said drive shaft, thus indicating the need for said head unit replacement.

* * * * *